United States Patent [19]
Guignard et al.

[11] Patent Number: 5,776,104
[45] Date of Patent: Jul. 7, 1998

[54] DEVICE FOR SUPPLYING A LIQUID TO A BODY CAVITY OF A PERSON OR AN ANIMAL AND SUBJECTING IT TO A DETERMINED PRESSURE

[76] Inventors: Mireille Guignard, "Le Vezely". Sergy-Gare. F-01630 Saint-Genis/Pouilly; Remi Cottenceau. "Les Hameaux de la Côte". La Côte. F-74580 Viry, both of France; Erwin Zuercher, Avenue du Lignon 21. CH-1219 Le Lignon, Switzerland

[21] Appl. No.: 553,531
[22] PCT Filed: Oct. 4, 1993
[86] PCT No.: PCT/FR93/00975
  § 371 Date: Nov. 30, 1995
  § 102(e) Date: Nov. 30, 1995
[87] PCT Pub. No.: WO94/27659
  PCT Pub. Date: Dec. 8, 1994

[30] Foreign Application Priority Data
  Jun. 1, 1993 [FR] France ................. 93 06627

[51] Int. Cl.$^6$ ........................... A61M 37/00
[52] U.S. Cl. ........................... 604/132; 604/131
[58] Field of Search ............. 604/131, 132, 604/192, 147, 190; 128/DIG. 12, DIG. 13

[56] References Cited

U.S. PATENT DOCUMENTS

| | | | |
|---|---|---|---|
| 2,693,801 | 11/1954 | Foreman | 604/147 |
| 3,404,748 | 10/1968 | Mamo | 604/147 X |
| 3,491,749 | 1/1970 | Gidlund | 604/147 X |
| 3,895,741 | 7/1975 | Nugent | |
| 4,657,160 | 4/1987 | Woods et al. | 604/147 X |
| 4,722,732 | 2/1988 | Martin | 604/132 |
| 4,741,733 | 5/1988 | Winchell et al. | 604/132 X |
| 5,019,037 | 5/1991 | Wang et al. | 604/147 X |
| 5,163,909 | 11/1992 | Stewart | |
| 5,536,245 | 7/1996 | McVay | 604/147 |

FOREIGN PATENT DOCUMENTS

| | | | |
|---|---|---|---|
| 0411 170 A1 | 2/1991 | European Pat. Off. | |
| 2 154 675 | 5/1973 | France | |
| 2 592 306 | 7/1987 | France | |
| 562287 | 6/1977 | U.S.S.R. | 604/147 |
| 563176 | 6/1977 | U.S.S.R. | 604/147 |
| 2 165 312 | 4/1986 | United Kingdom | |

*Primary Examiner*—Sam Rimell
*Attorney, Agent, or Firm*—Cushman Darby & Cushman IP Group of Pillsbury Madison & Sutro LLP

[57] ABSTRACT

A apparatus composed of a flexible bag containing a biological fluid in an enclosure sealed by a cover. The flexible bag is connected to a cavity in the human body through a tube that passes through a cover in the enclosure. In order to supply the biological fluid under an adjustable pressure to the cavity, the enclosure is connected to a source of pressurized air by means of an adjustable valve and a pressure regulator so that the pressure of the liquid in the cavity remains constant.

10 Claims, 3 Drawing Sheets

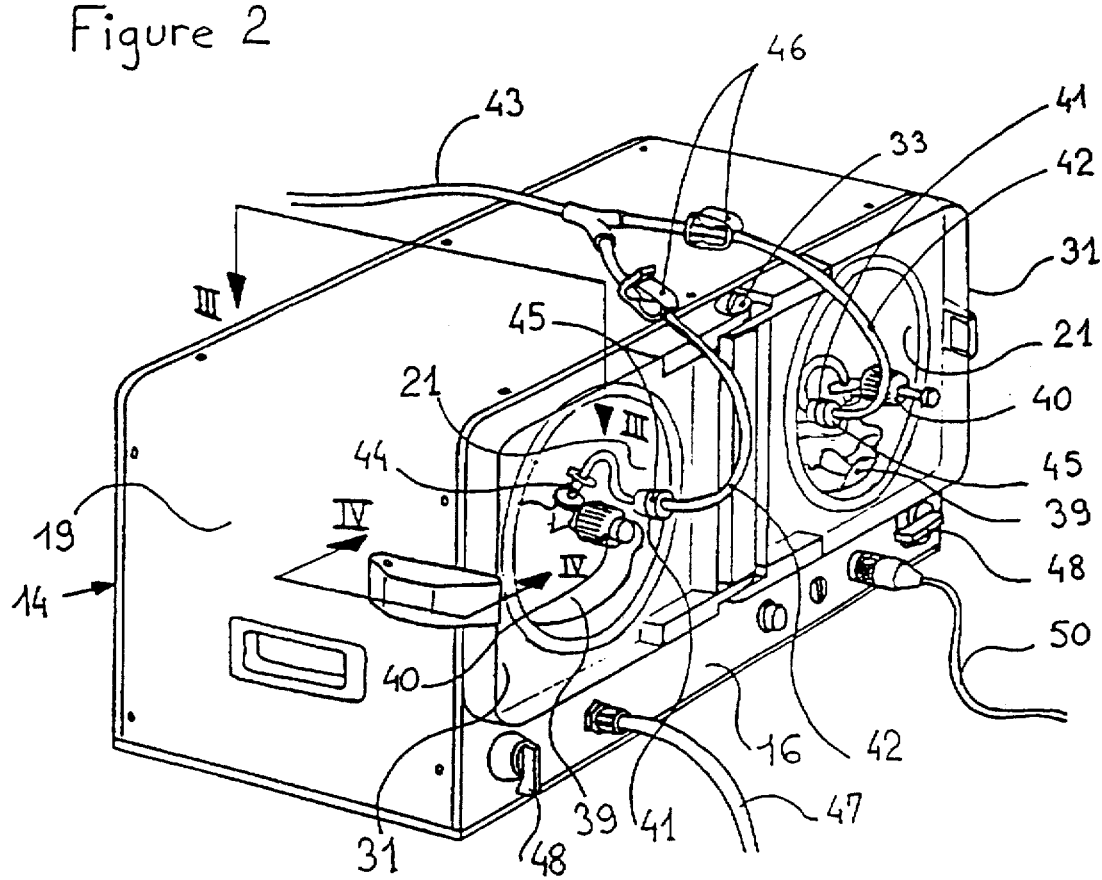
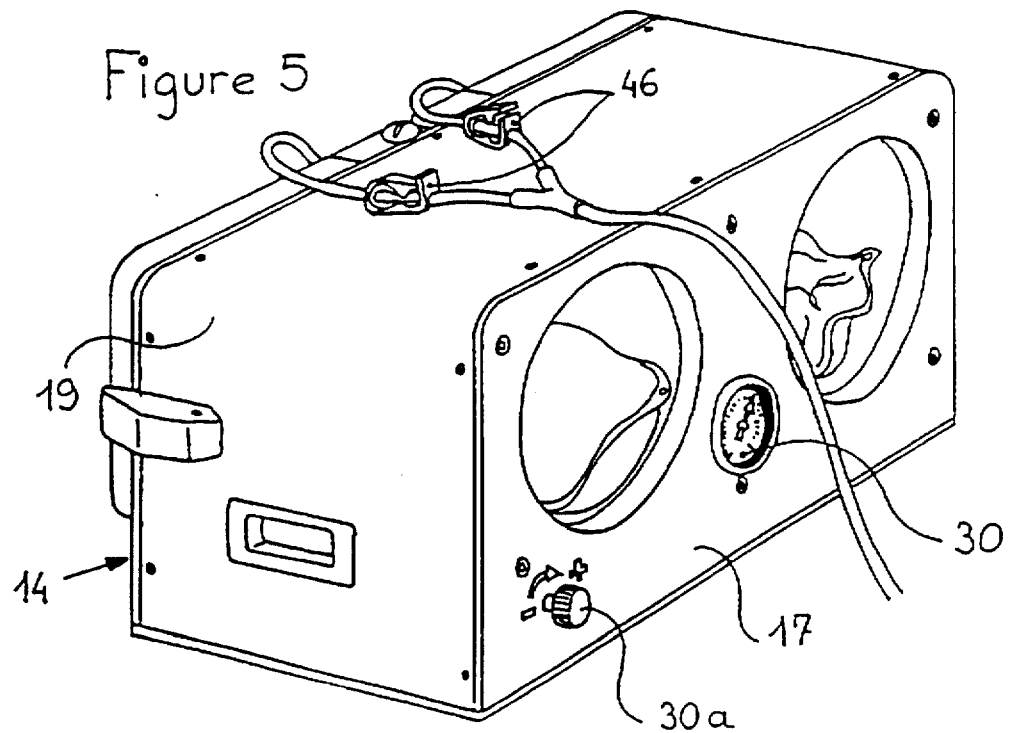

5,776,104

DEVICE FOR SUPPLYING A LIQUID TO A BODY CAVITY OF A PERSON OR AN ANIMAL AND SUBJECTING IT TO A DETERMINED PRESSURE

FIELD OF THE INVENTION

The present invention concerns a method and a device for supplying a liquid at a determined pressure to a body cavity of a person or an animal for the purpose of an endoscopic examination or operation, the liquid being supplied from a source contained in a watertight and sterile flexible bag, connected to the said cavity by a watertight and sterile tube.

BACKGROUND OF INVENTION

The number of endoscopic examinations and operations is growing constantly. In order to obtain a good image of the body's cavity to be observed or in which one wants to operate, one generally feeds biological liquid to this cavity, the role of which may be to inflate the cavity and to evacuate the material coming from a tissue resection which, otherwise, would quickly render the operating field opaque. The feed pressure is essentially variable, depending on the tissues forming the cavity to be observed or to be operated on. The maintenance of constant pressure is of great importance, as an increase as well as a decrease of pressure in the cavity can lead to serious repercussions for the patient. In fact, excessive pressure may cause infiltrations of the liquid into the patient's body and damage to the cavity itself. A depression can have other results which are just as serious. If, for instance, during the resection of a tumor on a bladder wall, done by means of electric resistance, a sudden decrease in pressure could, in an untimely manner, cause the bladder wall to come into contact with the heating element and be pierced, with all the serious consequences this would entail.

To measure the pressure of the liquid in the supply tube, a pressure sensor is installed in the supply tube. Such a sensor, however, poses a problem. One must, in fact, create a column of air in order to measure its pressure. To this end, the sensor must be installed at the end of a lateral tube, placed above the liquid level, and one measures the pressure of the air trapped in this lateral tube. To avoid any contact between the biological liquid and the sensor, a filter is installed at a certain distance from the sensor. The danger of this filter is that if it accidentally comes into contact with the liquid, some liquid will remain on the filter, and air bubbles will form in the tube, completely distorting the measurement. Since the risk of then seeing significant excessive pressure cannot be excluded, one must consider all the consequences that this would entail. The use of a security valve cannot be considered as, during the procedure, liquid could come into contact with nonsterile areas, which poses the risk of migration of microbial germs toward the irrigated cavity. Given these risks, some practitioners prefer to use the pressure created by a column of liquid, the height which is chosen according to the desired pressure. The drawback is that, depending on the desired pressure, there may not be enough vertical space in an operating room.

Until now, all irrigation devices operating with a pump used a peristaltic pump, which is the only pump in which no mechanical part come into contact with the liquid and is thus compatible with the sterility of the supply liquid. The drawback to these volumetric pumps is that sinusoidal pressure is created in the supply liquid. In some cases, this sinusoidal pressure variation is unacceptable, as in the case of an endoscopic operation on the uterine tube, where the pressure must be perfectly constant. Moreover, with a peristaltic pump equipped with a pressure sensor, there is always a reaction time, so the pressure can fluctuate, and, in reality, it fluctuates constantly.

SUMMARY OF INVENTION

The purpose of the present invention is to remedy these drawbacks, at least in part.

To this end, the purpose of the present invention is a method to supply a liquid at a determined pressure to a body cavity of a person or an animal, for the purpose of an endoscopic examination or operation, the liquid being supplied by a source contained in a watertight and sterile flexible bag, connected to the said cavity by a watertight and sterile tube, characterized by the fact that the said bag is then put in a watertight enclosure, and that this enclosure is connected to a source of fluid, the pressure of which is adjustable. Another purpose is a device to supply a liquid at a determined pressure to a body cavity of a person or an animal, for the purpose of an endoscopic examination or operation, consisting of at least one watertight and sterile flexible bag to contain the liquid to be supplied and a supply tube, connected to the said bag in a watertight and sterile fashion, characterized by the fact that it consists of at least one watertight enclosure in which the said bag is put and that this enclosure has an input port connected to a source of fluid under adjustable pressure and an opening for the watertight passage of the said supply tube though the wall of this enclosure.

The advantages of the method and the device, object of the invention, are numerous. The most important one springs from the fact that the displayed pressure is truly the pressure in the supply tube and the irrigated cavity, and that this pressure does not fluctuate. In the completely improbable event that excessive pressure should occur, one can make use of a security valve which is connected to the compression fluid and not the supply liquid, so that there is no risk of contamination of the supply liquid. The above-mentioned problems, linked to pressure measurement, no longer exist as it is the compression fluid's pressure which is being measured and not the supply liquid's. In addition to the great reliability of the device according to the invention, its great simplicity should also be pointed out, as one has but to connect the pressurization enclosure of the supply liquid to a source of pressurized air which exists in every operating room. The peristaltic supply pump's electronic servo-system, as well as the pump itself, are thus no longer necessary, substantially reducing the cost of the equipment.

BRIEF DESCRIPTION OF DRAWINGS

The appended drawing illustrates, schematically and as an example, one way to set up the device for supplying a liquid at a determined pressure to a body cavity of a person or an animal, object of the present invention.

FIG. 2 is a view in perspective of one setup, consisting of two parallel pressure enclosures.

FIG. 5 is a view in perspective of the side opposite the one in FIG. 2.

DETAILED DESCRIPTION OF PREFERRED EMBODIMENT

Figure 1:
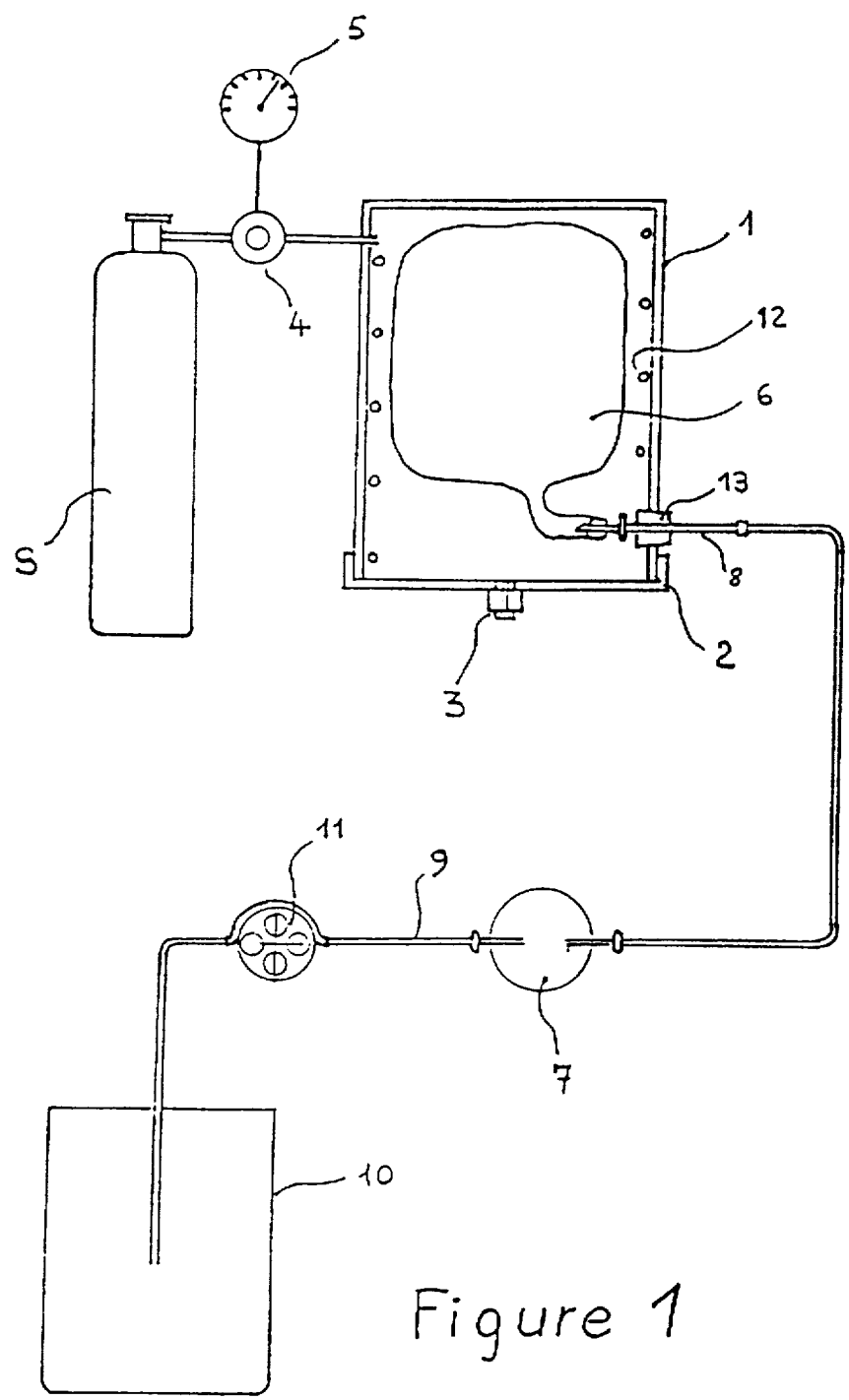
FIG. 1 is a schematic of this device.

This device is made up of a watertight enclosure 1, the walls of which are sufficiently rigid to resist the pressure which will be created in the enclosure. It is hermetically closed with a cover 2 equipped with a security valve 3, calibrated in function of the maximum acceptable pressure. The enclosure 1 is connected to a source of pressurized air S by means of a control valve 4 and a pressure regulator 5. This enclosure contains a flexible bag 6 containing the biological liquid to be used to irrigate a body cavity 7 of a person or an animal. A tube 8 goes through the wall of the enclosure 1 and is used to connect the flexible bag 6 to the cavity 7. A coniform joint 13 is used to ensure the water-tightness of the tube 8 through the wall of the enclosure 1. An outlet tube 9 connects this cavity to a recovery tank 10. A valve 11 or, preferably, a pump, is used to regulate the flow-rate in this tube 9, in function of the surgery or the examination being carried out by the practitioner. This outlet flow-rate is determined by the clarity of the liquid in the cavity which allows the practitioner to see the surgical field on a video screen, so that he can circulate a higher or lower flow-rate in function of the sharpness of the image which he observes on the screen.

Whatever the flow-rate is, the pressure in the enclosure 1, and thus in the flexible bag 6, the tube 8 and the cavity 7, is constant and corresponds to the one displayed on the pressure regulator 5. As the pressure regulator operates to maintain a constant pressure, it constantly adapts to the outlet flow-rate, as well as to leaks. If the pressure tends to lower, it immediately compensates for it. Should, for example, a solid body plug the outlet of the cavity 7, which can happen in the case of an endoscopic resection, there is no risk of an increase of pressure, even a temporary one, as the pressure will remain constant as long as the setting of the pressure regulator has not been modified. The security valve 3 is only there in the event that an adjusting mechanism should fail as, in fact, this would be the only risk of an abnormal pressure increase. It should be pointed out, moreover, that it was not possible to equip earlier irrigation systems with a security valve because of the risks of contamination, should the previously invoked valve be activated. Thanks to the method and device, object of the invention, the presence of this valve does not pose a problem, because it acts on the compression fluid and not on the irrigation circuit itself.

A heating element 12 may be installed in the enclosure 1, this heating element 12 being powered by a thermostatic adjustment mechanism (not shown).

Generally, the biological liquid for endoscopic surgery in the field of arthroscopy is set up in two bags connected to the same supply tube 8. In this case, one merely needs to provide for a second enclosure, identical to the enclosure 1, to hold the second bag.

In addition to the advantages mentioned previously, one can also point out that the device, object of the present invention, does not have any electric current except for the heating, which is limited to 40 W, which constitutes an advantage which cannot be overlooked.

As opposed to irrigation pumps of prior art, the reaction time is quasi instantaneous, while with the pumps known in the art, using a servo-system in function of the pressure, measured by compressing a column of air by the supply liquid, two causes of inertia are added. The first is the compression of the air in the column, the second is the repercussion time in the supply liquid from the time the order has been sent to the peristaltic pump. The clinical tests run, using the described device, clearly showed this advantage compared with irrigations systems known in the art.

The device illustrated by FIGS. 2 to 6 includes a housing 14, formed by a bottom 14, two opposed lateral walls 16 and 17, assembled by tie rods 18 also acting as a spacer frame, the internal space being closed by a cover 19, which is lodged on the two bearing surfaces 20 of the two opposed walls 16 and 17.

Figure 3:
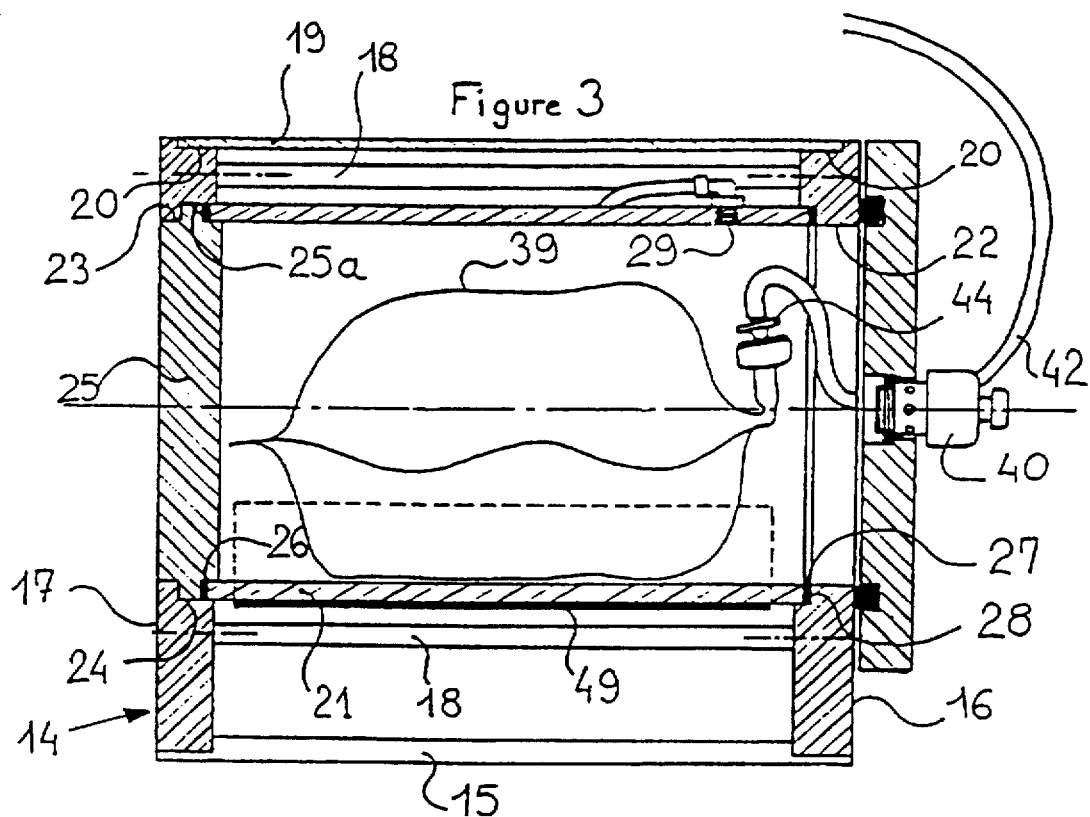
FIG. 3 is a cutaway view based on line III—III of FIG. 2.
Figure 4:
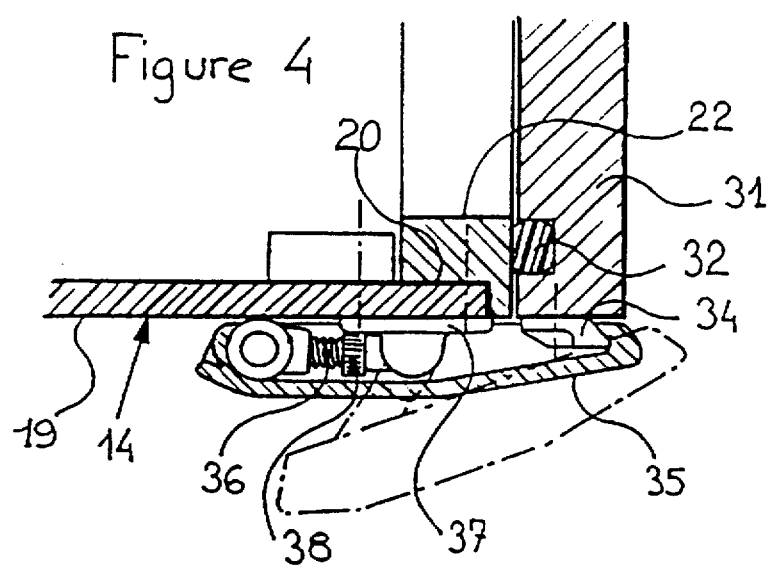
FIG. 4 is a cutaway view based on line IV—IV of FIG. 2.

Two cylinders 21 are mounted with their longitudinal axes disposed perpendicularly to the lateral walls 16 and 17. FIG. 3 shows the mounting of the cylinders 21 in the housing 14 in greater detail. The walls 16 and 17 are made up of plaques, each with two holes drilled through it, respectively 22 and 23, corresponding markedly to the internal diameter of the cylinders 21. The rear wall 17 presents an annular internal bearing surface 24, meant to hold a transparent disk 25, in plexiglass, for example. This disk 25 presents an annular part 25a which is set between the bearing surface 24 and a sealing gasket 26, compressed between one end of the cylinder 21 and the annular part 25a. The other end of the cylinder 21 compresses a sealing gasket 27 against an internal annular bearing surface 28 of the front wall 16, the assembly of the walls 16 and 17 and the cylinders being accomplished by the tie rods 18. Each cylinder 21 presents an opening 29 to allow the introduction of pressurized air. This air comes from a source of air compressed at 600 kPa and enters a precision manometer-pressure reducing valve 30 (FIG. 5), adjustable by means of a button 30a from which it emerges at the displayed pressure. In this example, it is a Festo (Germany) manometer-pressure reducing valve.

Each enclosure installed within the cylinders 21 is closed by a transparent door 31, in this example in plexiglass. The internal face of this door presents an annular groove in which a sealing gasket 32 is inserted. The lateral face of this door 31, opposed to its articulation hinge 33, presents a catch pin 34, while the fixed part of the housing bears a toggle type fastening mechanism including (FIG. 4) an articulated catch element 35 at the end of a rod 36, the other end of which is hinged to a base 37 which is part of the housing 14. The length of this rod 36 and thus, the space between the two hinge axes is adjustable thanks to a system with an adjustment screw 38. This closing system allows one to set the sealing gasket's 32 degree of compression. The open position of the catch element 35 has been illustrated in a dot-and-dash line.

As illustrated by FIG. 3, a watertight supply bag 39 containing biological liquid is put into each cylindrical enclosure. Each door 31 presents a security valve 40 set at 30 kPa in the event that the machine is used for endoscopic orthopedic surgery, as well as an opening 41 for the watertight passage of a feed tube 42. In this case, in a traditional manner, one has one Y tube made up of two tubes 42, each one leaving from one of the supply bags 39 and ending in a common supply tube 43 leading to the operating field. Each tube 42 ends in a striking pin 44 to pierce the supply bag 39. Between the striking pin 44 and the common tube 43, each tube presents a sealing plug 45 and a clamp 46, used to control the opening and closing of the tube 42.

FIG. 2 further illustrates a tube supplying compressed air 47 and a low voltage electric current (24 V) to heat the biological liquid, as well as valves 48 to start the pressurization to the value displayed by the manometer-pressure-reducing valve 30 of the cylindrical enclosures 21.

FIG. 3 further shows an electric resistance 49 for heating the biological liquid. This resistance 49 is buried in a plastic sheet stuck on the external face of the lower part of the cylinder 21. The heating is done by means of simple contact between the flexible bag 39, which hugs the form of the lower part of the cylinder 21, and the lower part of this cylinder. The resistance is calculated to increase the biological liquid's temperature by a factor of 18° to 20° C. compared with the ambient temperature, so that the temperature at the bag's outlet is approximately 42° C. so that, once the liquid arrives in the cavity to be irrigated, its temperature should be between 38° and 40° C.

Various interesting particularities of this machine may be brought up here. Its two lateral opposed walls are transparent, which allows both the surgeon and the theater nurse to check the level of the supply bag 39. Moreover, one of the transparent walls with the manometer-pressure-reducing valve 30 displaying the pressure and, if need be, allowing one to modify it thanks to the adjustment button 30a, may be turned toward the surgeon, who only has to be aware of the pressure and the fill level of the supply bag. The other opposed transparent wall is meant to be turned toward the theater nurse, who thus has access to the enclosures 21 through the transparent doors 31, which allows her to open and close the tubes 42 with the clamps 46 and, if need be, if two bags of biological liquid prove to be insufficient, to replace one.

To do so, she simply has to cut off the supply from the corresponding enclosure using the valve 48, to empty air from the enclosure by pulling on the corresponding security valve 40 and opening the door 31. She removes the strike pin 44 from the empty bag, removes the bag 39, replaces it with a full bag and pushes in the strike pin 44, closes the door 31 and opens the valve 48. This entire intervention is carried out without ever bothering the surgeon as it is done on the wall located, from his point of view, on the back of the machine.

The doors 31 are made of a thick plexiglass plaque, which gives it enough rigidity to attain watertightness with one single closing point.

The tubes 42, with the incorporated sealing plug, allow one to introduce the strike pin 44 through the opening 41 of the door 31 and to close this opening by pushing the plug 45 in.

The assembly of the front 16 and rear 17 walls with the help of the tie rods serving as spacers makes for an extremely simple assembly of the whole. The low voltage electric current with 40 W power allows the amperage to be reduced to below 2 A, so that the machine does not need electric accreditation. The cylinders, the cylindrical enclosures' floors and doors, all in plexiglass, enable good thermal insulation of the biological liquid.

The heating of the biological liquid by contact between the lower surface of the cylinders 21 and the supply bags 39 should also be mentioned. This type of heating without a water bath presents an important advantage. In fact, a water bath constitutes an ideal medium for the growth of germs. If any part of the connection between the supply bag 39 and the strike pin 44 should accidently come into contact with the water bath's water, there is a high risk of contamination, a risk which is avoided by the type of heating using the surface of cylinder 21, the external face of which is heated by the resistance 49.

We claim:

1. A device to facilitate endoscopic examination or operation by supplying a biological liquid to a body cavity of a person or an animal and thus pressurizing the cavity to a predetermined pressure, said device comprising:

at least one watertight and sterile flexible bag containing a biological liquid;

a watertight and sterile supply tube connecting said flexible bag to said cavity;

a means to pressurize said biological liquid supplied to said cavity, at a predetermined pressure;

an evacuation tube to empty said biological liquid from said cavity; and a means to adjust the flow rate through said evacuation tube, wherein, said means to pressurize said biological liquid supplied to said body cavity includes at least one watertight enclosure having rigid walls and enclosing said flexible bag, said enclosure having an access opening with watertight seal through which to insert and remove said flexible bag, said enclosure having an exit opening with a watertight seal for the exit of said supply tube from said enclosure, said enclosure having an entrance opening for introducing a source tube from a source of pressurized air, said source tube connecting said source to said watertight enclosure, and a means to adjust the pressure within said enclosure.

2. The device of claim 1, wherein said watertight enclosure further includes an adjustable security valve to release abnormally high pressure.

3. The device of claim 1, wherein said watertight enclosure further includes a thermoresistant heating mechanism.

4. The device of claim 1, further including a parallepipedic housing adapted to contain said device, said housing including:

two opposed transparent walls between which are two cylindrical enclosures, having two ends which are respectively adjacent to said opposed transparent lateral walls; sealing gaskets being located between said lateral walls and said ends of said cylindrical enclosures; one of said lateral walls having two doors, said doors respectively opening to each of said two cylindrical enclosures, said doors each having one exit opening with a watertight seal for the exit of a supply tube from each of said cylindrical enclosures, said supply tubes distally connecting to a single, common irrigation tube.

5. The device of clam 4, wherein said cylindrical enclosures are composed of thermal insulating material.

6. The device of claim 4, wherein each of said cylindrical enclosures has walls, parallel to the longitudinal axis of each of said enclosures, an external portion of each cylindrical enclosure wall being adjacent to a thermoresistant heating mechanism.

7. The device of claim 4, wherein each of said supply tubes at the end proximate to said flexible bag further includes a strike pin which pierces said bag, and wherein each of said supply tubes passes through a sealing plug between the strike pin and said single irrigation tube said sealing plug being located on each of said doors.

8. The device of claim 4, wherein each of said doors is closed by a toggle type fastening system.

9. The device of claim 4, further including a pressure adjustment manometer for regulating the pressure of said pressurized air from said pressurized air source, said manometer being located on said lateral transparent wall opposite said lateral transparent wall having said doors.

10. The device of claim 4, wherein said opposed, transparent lateral walls are fixed to each other by tie rods.

* * * * *